United States Patent [19]

Kashimura et al.

[11] Patent Number: 5,403,923
[45] Date of Patent: Apr. 4, 1995

[54] 6-0-METHYLERYTHROMYCIN A DERIVATIVES

[75] Inventors: Masato Kashimura, Omiya; Toshifumi Asaka, Kounosu; Shigeo Morimoto, Yoshikawa; Katsuo Hatayama, Omiya, all of Japan

[73] Assignee: Taisho Pharmaceutical Co., Ltd., Japan

[21] Appl. No.: 64,078

[22] PCT Filed: Nov. 22, 1991

[86] PCT No.: PCT/JP91/01608
  § 371 Date: May 20, 1993
  § 102(e) Date: May 20, 1993

[87] PCT Pub. No.: WO92/09614
  PCT Pub. Date: Jun. 11, 1992

[30] Foreign Application Priority Data

Nov. 28, 1990 [JP] Japan .................. 2-326529

[51] Int. Cl.$^6$ .................. C07H 17/08
[52] U.S. Cl. .................. 536/7.4; 536/7.2
[58] Field of Search .................. 536/7.2, 7.3, 7.4; 514/29

[56] References Cited

U.S. PATENT DOCUMENTS 4,640,910 2/1987 Faubl et al. .................. 514/29
4,742,049 5/1988 Baker et al. .................. 514/29

FOREIGN PATENT DOCUMENTS 2184921 6/1986 European Pat. Off. .
0248279 5/1987 European Pat. Off. .
0321185 12/1988 European Pat. Off. .

OTHER PUBLICATIONS

Journal of Organic Chemistry, vol. 53, No. 10 pp. 2340 to 2345, Baker et al.

Primary Examiner—John W. Rollins
Assistant Examiner—Elli Peselel
Attorney, Agent, or Firm—Lorusso & Loud

[57] ABSTRACT

This invention provides 6-O-methylerythromycin A derivatives represented by the following formula (wherein $R^1$ and $R^2$ each represent a hydrogen atom or an alkyl group having 1 to 3 carbon atoms, and A represents a nitrogen atom or a N→O group) and their pharmaceutically acceptable salts. The erythromycin A derivatives have a strong antimicrobial activity against Gram-negative bacteria and have a much stronger activity against Gram-positive bacteria than previously known compounds.

1 Claim, No Drawings

6-0-METHYLERYTHROMYCIN A DERIVATIVES

TECHNICAL FIELD

This invention relates to antibiotics for use in chemotherapy of infectious diseases by bacteria, and more detailedly to erythromycin A derivatives exhibiting a high antimicrobial activity also against Gram-negative bacteria, their pharmaceutically acceptable salts and intermediates for preparation thereof.

1. Background Art

A macrolide antibiotic erythromycin A exhibits a desirable antimicrobial activity against many Gram-positive bacteria, mycoplasmas, etc., and is clinically and widely used. However, erythromycin A has only a weak antimicrobial activity against Gram-negative bacteria, and it was impossible to expect a sufficient therapeutic effect.

The object of this invention lies in providing novel erythromycin A derivatives having a strong antimicrobial activity against Gram-negative bacteria, and having against Gram-positive bacteria also a much stronger effect than compounds so far known.

2. Disclosure of Invention

The present inventors found that novel compounds having a tricyclic basic nuclear structure obtained by combining the 11- and 12-positions of 6-O-methylerythromycin A to give a cyclic carbamate compound, and further by combining the nitrogen atom of the carbamate with the 9-position through an ethylene chain or a substituted ethylene chain to give a cyclic imine compound or a nitron compound, not only exhibit a strong antimicrobial activity against Gram-positive bacteria, but also exhibit a strong antimicrobial activity against Gram-negative bacteria, and completed this invention.

Thus, this invention relates to 6-O-methyl-erythromycin A derivatives represented by the following formula (I)

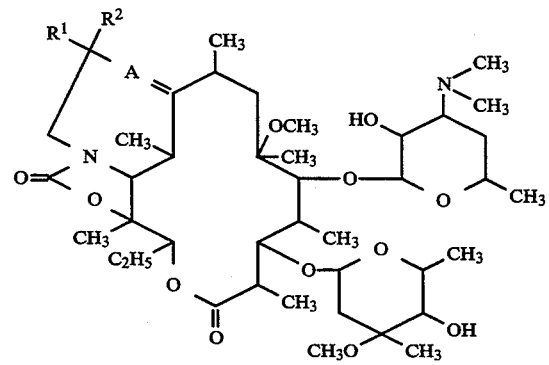

(wherein $R^1$ and $R^2$ each represent a hydrogen atom or an alkyl group having 1 to 3 carbon atoms, and A represents a nitrogen atom or a N→O group) and their pharmaceutically acceptable salts, and compounds represented by the following formula (II), which are intermediates for preparation of the compounds of the formula (I)

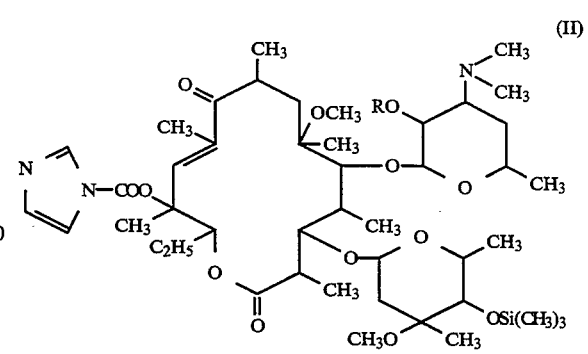

(wherein R represents an acetyl group or a trimethylsilyl group).

As pharmaceutically acceptable salts in this invention, there can, for example, be mentioned acetates, propionates, butyrates, formates, trifluoroacetates, maleates, tartrates, citrates, stearates, succinates, ethylsuccinates, lactobionates, gluconates, glucoheptonates, benzoates, methanesulfonates, ethanesulfonates, 2-hydroxyethanesulfonates, benzenesulfonates, p-toluenesulfonates, lauryl sulfates, malates, aspartates, glutamates, adipates, cysteine salts, hydrochlorides, hydrobromides, phosphates, sulfates, hydroiodides, nicotinates, oxalates, picrates, thiocyanates, undecanoates, acrylic acid polymer salts, carboxyvinyl polymer salts, etc.

The compounds of the formula (I) of this invention can, for example, be prepared as follows from the compounds of the formula (II).

That is, (1) first, a compound of the formula (II) can be reaction with a diamine represented by the following formula (III)

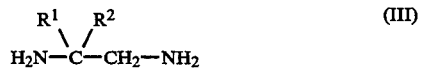

(wherein $R^1$ and $R^2$ are as defined above) in a suitable solvent (for example, acetonitrile, tetrahydrofuran or a mixture thereof, or the like) to give a compound represented by the following formula (IV)

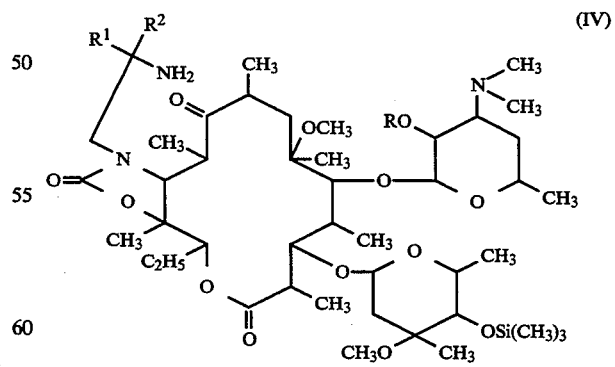

(wherein $R^1$ and $R^2$ are as defined above, and R is a trimethylsilyl group or an acetyl group).

(2) Then, the compound of the formula (IV) can be treated with tetranormalbutylammonium fluoride or a suitable acid (for example, formic acid, acetic acid or the like) to remove the trimethylsilyl group, or in case of a compound of the formula (IV) wherein R is an acetyl group, the compound can be heat treated in methanol to remove the acetyl group, and then the resultant compound can be boiled with a small excessive amount of acetic acid in ethanol to give a compound of this invention of the formula (I) wherein A is a nitrogen atom.

When an acid is used for the detrimethylsilylation, there is a case where cyclization reaction to the 9-position takes place at the same time with the detrimethylsilylation to give a compound of this invention of the formula (I) wherein A is a nitrogen atom.

(3) A compound of the formula (I) wherein A is a N→O group can be obtained by oxidizing a compound of the formula (I) wherein A is a nitrogen atom with m-chloroperbenzoic acid, and regenerating the dimethylamino group which was oxidized at the 3'-position, by use of triphenylphosphine.

Incidentally, the compounds of the formula (II) as a starting substance are novel compounds, and can be prepared from 6-O-methylerythromycin A by the following processes.

(1) In case of a compound of the formula (II) wherein R is a trimethylsilyl group Such a compound can be obtained by reacting, first, 6-O-methylerythromycin A with a trimethylsilylating agent [for example, 1,1,1,3,3,3-hexamethyldisilazane, trimethylchlorosilane, bis(trimethylsilyl)acetamide or the like] to give 2',4''-O-bis-trimethylsilyl-6-O-methylerythromycin A, and then reacting it with an excessive amount of N,N'-carbonyldiimidazole and a suitable base (for example, sodium hydride, sodium bistrimethylsilylamide or the like) at room temperature in a suitable solvent (for example, N,N-dimethylformamide, N-methylpyrrolidone, tetrahydrofuran, acetonitrile or a mixed solvent thereof, or the like).

(2) In case of a compound of the formula (II) wherein R is an acetyl group

2'-O-Acetyl-10,11-anhydro-4''-O-trimethylsilyl-6-O-methylerythromycin A can be obtained by reacting 6-O-methylerythromycin A with ethylene carbonate and potassium carbonate to give 10,11-anhydro-6-O-methylerythromycin A, reacting this with acetic anhydride and potassium carbonate to 2'-O-acetylate, and then reacting the resultant compound with a small excessive amount of pyridine and trimethylchlorosilane in methylene chloride. The obtained 2'-O-acetyl-10,11-anhydro-4''-O-trimethylsilyl-6-O-methylerythromycin A can be reacted with N,N'-carbonyldiimidazole and a suitable base (for example, sodium hydride, sodium bis-trimethylsilylamide or the like) in a suitable solvent (for example, N,N-dimethylformamide, N-methylpyrrolidone, tetrahydrofuran, acetonitrile or a mixed solvent thereof, or the like) at room temperature to give a compound of the formula (II) wherein R is an acetyl group.

The compounds of the formula (I) of this invention can be formulated into dosage forms such as tablets, capsules, powders, troches, ointments, suspensions or solutions, and can be administered orally or parenterally. The above preparations can be prepared by a conventional method (for example, a method prescribed in the Japanese Pharmacopoeia XII) using conventional excipients (for example, crystalline cellulose, starch, lactose, etc.), binders (for example, hydroxypropylcellulose, polyvinylpyrrolidone, etc.), lubricants (for example, magnesium stearate, talc, etc.), etc. The dose of a compound of the formula (I) differs depending on the symptom, age and weight of the patient, etc., but is usually 50 to 2,000 mg per day for an adult, and the compound is administered per day in single or up to four divided doses.

BEST MODE OF CARRYING OUT THE INVENTION

This invention is described in more detail below by examples and test examples.

EXAMPLE 1

Preparation of 11-amino-9-N,11-N-cyclic ethylene-9-deoxo-11-deoxy-6-O-methylerythromycin A 9-imine 11-N,12-O-cyclic carbamate (1) 20.0 g (26.7 mmoles) of 6-O-methylerythromycin A was dissolved in 200 ml of N,N-dimethylformamide, 1.43 g (26.7 mmoles) of ammonium chloride was added, 14.1 ml (66.8 mmoles) of 1,1,1,3,3,3-hexamethyldisilazane was added dropwise at room temperature, and the mixture was stirred as such for 3 hours. Water was poured into the reaction solution, and the mixture was extracted with ethyl acetate. The organic layer was washed with water and saturated saline, and dried over anhydrous magnesium sulfate. After distilling off ethyl acetate under reduced pressure, crystallization was carried out from acetonitrile to give 22.4 g of 2',4''-O-bis(-trimethylsilyl)-6-O-methylerythromycin A.

m.p. 106°–108° C. and 177°–180° C.

(2) 20.3 g (22.8 mmoles) of the compound obtained in the above (1) and 18.5 g (114.1 mmoles) of N,N'-carbonyldiimidazole were dissolved in 200 ml of a mixed solvent of N,N-dimethylformamide/tetrahydrofuran (3/1), 3.0 g (75.0 mmoles) of 60% sodium hydride was added under water cooling, and the mixture was stirred as such for 15 minutes. Water was poured into the reaction solution, and the mixture was extracted with ethyl acetate. The organic layer was washed with water and saturated saline and dried over anhydrous magnesium sulfate. Ethyl acetate was distilled off under reduced pressure, and crystallization was carried out from acetonitrile to give 21.8 g of 10,11-anhydro-12-O-imidazolylcarbonyl-2',4''-O-bis(trimethylsilyl)-6-O-methylerythromycin A.

m.p. 155°~158° C.

Mass (FAB) m/z; 968 [MH]+

$^1$H-NMR (300 MHz, CDCl$_3$) δ ((ppm); 0.04 (9H.TMS), 0.17 (9H.TMS), 2.21 [6H.3'-N(CH$_3$)$_2$], 3.26 (3H, 6-OCH$_3$), 3.31 (3'-OCH$_3$), 6.79 (1H, 11), 7.06, 7.37, 8.08 (3 H, imidazole)

$^{13}$C-NMR (75 MHz, CDCl$_3$) δ (ppm); 0.9 (TMS), 1.0 (TMS), 40.8 [3'-N(CH$_3$)$_2$], 49.8 (3'-OCH$_3$), 51.0 (6-OCH$_3$), 117.2, 130.9, 137.0 (imidazole), 138.5 (11), 145.9 (12—OCO—)

(3) 20.1 g (20.8 mmoles) of the compound obtained in the above (2) was dissolved in 200 ml of a mixed solvent of acetonitrile/tetrahydrofuran (4/1), 13.9 ml (207.9 mmoles) of ethylenediamine was added, and the mixture was stirred at 50° C. for 2 hours. The solvent was distilled off under reduced pressure, water was added to the residue, and the mixture was extracted with ethyl acetate. The organic layer was washed with water and saturated saline, and dried over anhydrous magnesium sulfate. Ethyl acetate was distilled off under reduced pressure to give 22.0 g of a white foamy substance. This substance then dissolved in 200 ml of tetrahydrofuran, 7.3 g (27.9 mmoles) of tetranormalbutylammonium fluoride was added, and the mixture was stirred at room temperature for 2 hours. The solvent was distilled under reduced pressure, a 2N sodium hydroxide solution and water were poured into the residue, and the mixture was extracted with chloroform. The organic layer was washed with water and saturated saline, and dried over anhydrous magnesium sulfate. Chloroform was distilled off under reduced pressure to obtain 19.1 g of 11-(2-amino)ethylamino-11-deoxy-6-O-methylerythromycin A 11-N,12-O-cyclic carbamate as a white foamy substance.

(4) 17.0 g (20.9 mmoles) of the compound obtained in the above (3) was dissolved in 170 ml of ethanol, 1.8 ml (31.4 mmoles) of acetic acid was added, and the solution was refluxed for 3.5 hours by heating. After the reaction, the solvent was distilled off under reduced pressure, a 2N sodium hydroxide solution and water were poured into the residue, and the mixture was extracted with chloroform. The organic layer was washed with water and saturated saline, and dried over anhydrous magnesium sulfate. Chloroform was distilled off under reduced pressure, and the residue was crystallized using a mixed solvent of ethyl acetate-dichloromethane to give 13.5 g of the captioned compound as white crystals.

m.p. 253°~255° C.
Mass (FAB) m/z: 798 [MH]+
$^1$H-NMR (300 MHz, CDCl$_3$) δ (ppm): 2.29 [6H, 3'-N(CH$_3$)$_2$], 3.09 (3H, 6-OCH$_3$), 3.33 (3H, 3'-OCH$_3$)
$^{13}$C-NMR (75 MHz, CDCl$_3$) δ (ppm): 40.4 [3'-N(CH$_3$)$_2$], 42.5 (NCH$_2$), 49.5 (NCH$_2$, 3'-OCH$_3$), 50.1 (6-OCH$_3$), 156.3 (NCOO), 182.8 (9)

EXAMPLE 2

Preparation of 11-amino-9-N,11-N-cyclic(1-methyl)ethylene-9-deoxo-11-deoxy-6-O-methylerythromycin A 9-imine 11-N,12-O-cyclic carbamate (1) 50 g (67 mmoles) of 6-O-methylerythromycin A was dissolved in 600 ml of N,N-dimethylformamide, 100 g (1.1 moles) of ethylene carbonate and 100 g (0.72 mole) of potassium carbonate were added, and the mixture was stirred at 90° C. for 21 hours. After the reaction, 6,000 ml of water was poured into the reaction solution, and the precipitate was taken by filtration. The precipitate was then dissolved in 1,000 ml of ethyl acetate, and the organic layer was washed with saturated saline and dried over anhydrous magnesium sulfate. The solvent was distilled off under reduced pressure, and crystallization was carried out from acetone to give 21.7 g of 10,11-anhydro-6-O-methylerythromycin A.

m.p. 256°~258° C.
Mass (SIMS) m/z; 730 [MH]+
$^1$H-NMR (400 MHz, CDCl$_3$) δ (ppm): 2.00 (3H, 10-CH$_3$), 2.27 [6H, 3'-N(CH$_3$)$_2$], 3.24 (3H, 6-OCH$_3$), 3.31 (3H, 3'-OCH$_3$)
$^{13}$C-NMR (100 MHz, CDCl$_3$) δ (ppm); 20.8 (6-CH$_3$), 40.2 [3'-N (CH$_3$)$_2$], 49.4 (3'-OCH$_3$), 50.7 (6-OCH$_3$), 78.4 (6), 138.7 (11), 142.5 (10), 175.1 (1), 207.3 (9)

(2) 25 g (34.3 mmoles) of the compound obtained above was dissolved in 290 ml of a mixed solvent of acetone/dichloromethane (3/1), 14.2 g (102.7 mmoles) of potassium carbonate and 6.48 ml (38.6 mmoles) of acetic anhydride were added, and the mixture was stirred at room temperature for 2 hours. The reaction solution was filtered, and the insoluble matters were washed with acetone. The filtrate and the washings were combined and concentrated under reduced pressure, a 2N sodium hydroxide solution and water were poured into the resultant residue, and the mixture was extracted with ethyl acetate. The organic layer was washed with water and then saturated saline, and dried over anhydrous magnesium sulfate. The solvent was distilled off under reduced pressure to give 2'-O-acetyl-10,11-anhydro-6-O-methylerythromycin A as a white foamy substance.

$^1$H-NMR (200 MHz, CDCl$_3$) δ (ppm); 2.05 (3H, 2'-OCOCH$_3$), 2.30 [6H, 3'-N (CH$_3$)$_2$], 3.15 (3H, 6-OCH$_3$), 3.35 (3 H, 3'-OCH$_3$), 6.53 (1H, 11).

The obtained white foamy substance was dissolved in 200 ml of dichloromethane, 7.37 ml (91.1 mmoles) of pyridine and 8.7 ml (68.5 mmoles) of trimethylchlorosilane were added, and the mixture was stirred at room temperature for 1 hour. Water was poured into the reaction solution, the mixture was shaked sufficiently, and then the water layer and the organic layer were separated. The organic layer was concentrated under reduced pressure, ethyl acetate was added to the resultant residue, the mixture was sufficiently washed with water, and the organic layer was washed with saturated saline and dried over anhydrous magnesium sulfate. The solvent was distilled off under reduced pressure, and the resultant residue was crystallized from acetonitrile to give 20.4 g of 2'-O-acetyl-10,11-anhydro-4"-O-trimethylsilyl-6-O-methylerythromycin A as white crystals. Further, the filtrate at the time of the crystallization was concentrated, and then subjected to purification by silica gel column chromatography (acetone: n-hexane: triethylamine=3:10:0.2) to give further 4.7 g of the above compound.

$^1$H-NMR (300 MHz, CDCl$_3$) δ (ppm); 0.15 (9H, 4'-OTMS), 2.34 [6H, 3'-N(CH$_3$)$_2$], 3.15 (3H, 6-OCH$_3$), 3.33 (3H, 3'-OCH$_3$), 6.52 (1H, 11)

(3) 20.4 g (24.2 mmoles) of the compound obtained in the above (2) was dissolved in 220 ml of a mixed solvent of N,N-dimethylformamide/tetrahydrofuran (10/1), 19.6 g (120.9 mmoles) of N,N'-carbonyldiimidazole and 1.16 g (29.0 mmoles) of 60% sodium hydride were added at room temperature, and the mixture was kept stirring as such for 10 minutes. A 2N sodium hydroxide solution and water were poured into the reaction solution, and the mixture was extracted with ethyl acetate. The organic layer was washed with water and then saturated saline, and dried over anhydrous magnesium sulfate. The solvent was distilled off under reduced pressure to give 22.2 g of 2'-O-acetyl-10,11-anhydro-12-O-imidazolylcarbonyl-4"-O-trimethylsilyl-6-O-methylerythromycin A as a white foamy substance.

Mass (FAB) m/z; 938 [MH]+
$^1$H-NMR (300 MHz, CDCl$_3$) δ (ppm); 0.17 (9H, 4'-OTMS), 2.29 [6H, 3'-N(CH$_3$)$_2$], 3.12 (3H, 6-OCH$_3$), 3.32 (3H, 3'-OCH$_3$), 6.65 (1H, 11), 7.06, 7.36, 8.08 (3H, imidazole)
$^{13}$C-NMR (75 MHz, CDCl$_3$) δ (ppm); 0.9 (4'-OTMS), 40.6 [3'-N(CH$_3$)$_2$], 49.7 (3'-OCH$_3$), 50.7 (6-OCH$_3$), 145.8 (12-OCO), 170.0 (2'-OCOCH$_3$)

(4) 1.0 g (1.1 mmoles) of the compound obtained in the above (3) as dissolved in 10 ml of acetonitrile, 0.91 ml (10.7 mmoles) of 1,2-diaminopropane was added, and the mixture was stirred at 50° C. for 3.5 hours. After the reaction, the solvent was distilled off under reduced pressure, water was added to the residue, and the mixture was extracted with ethyl acetate. The organic layer was washed with water and then saturated saline, and dried over anhydrous magnesium sulfate. The solvent was distilled off under reduced pressure to give a white foamy substance. This substance was then dissolved in 10 ml of methanol, and the solution was refluxed for 3 hours by heating. Methanol was distilled off under reduced pressure, 10 ml of ethanol and 0.08 ml 2.1 mmoles) of 99% formic were added to the resultant residue, and the solution was refluxed for 3 hours by heating. Ethanol was distilled off under reduced pressure, a 2N sodium hydroxide solution and water were poured into the resultant residue, and the mixture was extracted with ethyl acetate. The organic layer was washed with water and then saturated saline and dried over anhydrous magnesium sulfate. The solvent was distilled off under reduced pressure, and the resultant residue was purified by silica gel column chromatography (chloroform: methanol: ammonia water=20:1:0.1) to give 0.28 g of the captioned compound.

m.p. 251°~254° C. (crystallized from ethyl acetate-n-hexane)

Mass (FAB) m/z; 812 [MH]+

$^1$H-NMR (300 MHz, CDCl$_3$) δ ((ppm); 2.30 [6H, 3'-N(CH$_3$)$_2$], 3.08 (3H, 6-OCH$_3$), 3.33 (3H, 3'-OCH$_3$)

$^{13}$C-NMR (75 MHz, CDCl$_3$) δ (ppm); 22.9 [9-NCH(CH$_3$)CH$_2$N], 40.3 [3'-N(CH$_3$)$_2$], 48.3 [9-NCH(CH$_3$)CH$_2$N], 49.5 (3'-OCH$_3$), 49.9 (6-OCH$_3$), 53.4 [9-NCH(CH$_3$)CH$_2$N], 178.8 (9)

EXAMPLE 3

Preparation of 11-amino-9-N,11-N-cyclic (1-methyl)ethylene-9-deoxo-11-deoxy-6-O-methylerythromycin A 9-imine 11-N, 12-O-cyclic carbamate [Preparation of one epimer on the cyclic ethylene part of the compound obtained in Example 2 (4)]

(1) 3.0 g (3.1 mmoles) of the compound obtained in (2) of Example 1 was dissolved in 40 ml of acetonitrile/tetrahydrofuran (3/1), 2.64 ml (31.0 mmoles) of 1,2-diaminopropane was added, and the mixture was stirred at 50° C. for 5 hours. After the reaction, the solvent was distilled off under reduced pressure, water was poured into the residue, and the mixture was extracted with ethyl acetate. The organic layer was washed with water and then saturated saline, and dried over anhydrous magnesium sulfate. The solvent was distilled off under reduced pressure to give a white foamy substance. This substance was then dissolved in 30 ml of tetrahydrofuran, 1.22 g (4.6 mmoles) of tetranormalbutylammonium fluoride was added, and the mixture was stirred at room temperature for 1 hour. After the same treatment as previously stated was carried out, purification was made by silica gel column chromatography (chloroform: methanol: ammonia water=20:1:0.1) to give 1.1 g of the compound obtained in (4) of Example 2 and 1.3 g of 11-(2-aminopropyl)amino-11-deoxy-6-O-methylerythromycin A 11-N,12-O-cyclic carbamate as a white foamy substance.

$^1$H-NMR (300 MHz, CDCl$_3$) δ (ppm); 2.30 [6H, 3'-N(CH$_3$)$_2$], 3.04 (3H, 6-OCH$_3$), 3.33 (3H, 3'-OCH$_3$)

(2) 1.1 g (1.3 mmoles) of the compound obtained in the above (1) was dissolved in 10 ml of ethanol, 0.11 ml (1.9 mmoles) of acetic acid was added, and the solution was refluxed for 27 hours by heating. After the reaction, the solvent was distilled off under reduced pressure, a 2N sodium hydroxide solution and water were poured into the residue, and the mixture was extracted with chloroform. The organic layer was washed with water and then saturated saline, and dried over anhydrous magnesium sulfate. The solvent was distilled off under reduced pressure, and purification was made by silica gel column chromatogaphy (chloroform: methanol: ammonia water=20:1:0.1) to give 0.68 g of the captioned compound.

m.p. 246°~249° C. (crystallized from ethyl acetate-n-hexane)

Mass (FAB) m/z: 812 [MH]+

$^1$H-NMR (300 MHz, CDCl$_3$) δ (ppm); 2.28 [6H, 3'-N(CH$_3$)$_2$], 3.06 (3H, 6-OCH$_3$), 3.33 (3H, 3'-OCH$_3$)

$^{13}$C-NMR (75 MHz, CDCl$_3$) δ (ppm); 40.3 [3'-N(CH$_3$)$_2$], 48.2 [9-NCH(CH$_3$)CH$_2$N], 49.5 (3'-OCH$_3$), 50.2 (6-OCH$_3$), 55.1 [9-NCH(CH$_3$)CH$_2$N], 177.6 (9)

EXAMPLE 4

Preparation of 11-amino-9-N,11-N-cyclic(1,1-dimethyl)ethylene-9-deoxo-11-deoxy-6-O-methylerythromycin A 9-imine 11-N, 12-O-cyclic carbamate (1) 2 g (2.2 mmoles) of the compound obtained in (3) of Example 2 was dissolved in 20 ml of acetonitrile, 2.24 ml (21.4 mmoles) of 1,2-diamino-2-methylpropane was added, and the mixture was stirred at 50° C. for 6 hours and further stirred at room temperature for 15 hours. After the reaction, the solvent was distilled off under reduced pressure, water was poured into the residue, and the mixture was extracted with ethyl acetate. The organic layer was washed with water and then saturated saline, and dried over anhydrous magnesium sulfate. The solvent was distilled off under reduced pressure to give a white foamy substance. This substance was then dissolved in 20 ml of methanol, and the solution was refluxed by heating for 4 hours. 0.2 ml (5.3 mmoles) of 99% formic acid was added to the reaction solution, and the mixture was then refluxed with heating for 2 hours. Methanol was distilled off under reduced pressure, a 2N sodium hydroxide solution and water were poured into the resultant residue, and the mixture was extracted with chloroform. The organic layer was washed with water and then saturated saline, and dried over anhydrous magnesium sulfate. The solvent was distilled off under reduced pressure, and the resultant residue was crystallized from a mixed solvent of ethyl acetate and dichloromethane to give 1.13 g of 11-(2-amino-2 -methyl)propylamino-11-deoxy-6-O-methylerythromycin A 11-N, 12-O-cyclic carbamate.

Mass (FAB) m/z; 844 [MH]+

$^1$H-NMR (300 MHz, CDCl$_3$) δ (ppm); 2.28 [6H, 3'-N(CH$_3$)$_2$], 3.03 (3H, 6-OCH$_3$), 3.32 (3H, 3'-OCH$_3$)

$^{13}$C-NMR (75 MHz, CDCl$_3$) δ (ppm); 40.3 [3'-N(CH$_3$)$_2$], 49.5 (3'-OCH$_3$), 51.1 (6-OCH$_3$), 52.0 [9-NC(CH$_3$)$_2$CH$_2$]

(2) 1.0 (1.0 mmole) of the compound obtained in the above (1) was dissolved in 10 ml of ethanol, 0.14 ml (2.4 mmoles) of acetic acid was added, and the mixture was refluxed by heating for 40 hours. Ethanol was distilled off under reduced pressure, a 2N sodium hydroxide solution and water were poured into the residue, and the mixture was extracted with chloroform. The organic layer was washed with water and then saturated saline, and dried over anhydrous magnesium sulfate. The solvent was distilled off under reduced pressure to give a white foamy substance. This was purified by silica gel column chromatography (chloroform: methanol: ammonia water=20:1:0.1) to give 0.59 g of 11-amino-9-N,11-N-cyclic(1,1-dimethyl)ethylene-9-deoxo-11-deoxy-6-O-methylerythromycin A 9-imine 11-N,12-O-cyclic carbamate.

m.p. 151°~154° C. (crystallized from acetonitrile)

Mass (FAB) m/z; 826 [MH]+

$^1$H-NMR (300 MHz, CDCl$_3$) δ (ppm); 2.29 [6H, 3'-N(CH$_3$)$_2$], 3.09 (3H, 6-OCH$_3$), 3.33 (3H, 3'-OCH$_3$)

$^{13}$C-NMR (75 MHz, CDCl$_3$) δ (ppm); 40.3 [3'-N(CH$_3$)$_2$], 49.5 (3'-OCH$_3$), 50.1 (6-OCH$_3$), 58.7 [9-NC(CH$_3$)$_2$CH$_2$], 175.6 (9)

EXAMPLE 5

Preparation of 11-amino-9-N,11-N-cyclic ethylene-9-deoxo-11-deoxy-6-O methylerythromycin A 9-imine 11-N, 12-O-cyclic carbamate 9-N-oxide (1) 1.0 g (1.3 mmoles) of the compound obtained in (4) of Example 1 was dissolved in 10 ml of chloroform, 863 mg (5.0 mmoles) of m-chloroperbenzoic acid was added, and the mixture was stirred at room temperature for 1 hour. A 2N sodium hydroxide solution and water were poured into the reaction solution, and after extraction, the organic layer was washed with water and saturated saline and the dried over anhydrous magnesium sulfate. The solvent was distilled off under reduced pressure to give 1.06 g of 11-amino-9-N, 11-N-cyclic ethylene-9-deoxo-11-deoxy-6-O-methylerythromycin A 9-imine 11-N, 12-O-cyclic carbamate 9,3'-bis-N-oxide as a white foamy substance.

Mass (FAB) m/z; 830 [MH]+

$^1$H-NMR (300 MHz, CDCl$_3$) δ (ppm); 3.19 (3H, 6-OCH$_3$) , 3.22, 3.27 [6H, 3'-N(CH$_3$)$_2$], 3.36 (3H, 3'-OCH$_3$)

$^{13}$C-NMR (75 MHz, CDCl$_3$) δ (ppm); 49.6 (3'-OCH$_3$), 51.2 (6-OCH$_3$), 52.1, 59.0 [3'-N(CH$_3$)$_2$]

(2) 0.8 g (0.97 mmoles) of the compound obtained in the above (1) was dissolved in 5 ml of tetrahydrofuran, 1.01 g (3.9 mmoles) of triphenylphosphine was added, and the mixture was refluxed by heating for 4 hours. The solvent was distilled off under reduced pressure, a 2N sodium hydroxide solution and water were poured on the residue, and the mixture was extracted with ethyl acetate. The organic layer was washed with water and saturated saline, and dried over anhydrous magnesium sulfate. The solvent was distilled off under reduced pressure, and the resultant residue was crystallized from a mixed solvent of ethyl acetate/n-hexane to give 0.52 g of the captioned compound as white crystals.

m.p. 255°~258° C.

Mass (FAB) m/z; 814 [MH]+

$^1$H-NMR (300 MHz, CDCl$_3$) δ (ppm); 2.29 [6H, 3'-N(CH$_3$)$_2$], 3.20 (3H, 6-OCH$_3$), 3.33 (3H, 3'-OCH$_3$)

$^{13}$C-NMR (75 MHz, CDCl$_3$) δ (ppm); 40.3 [3'-N(CH$_3$)$_2$], 49.5 (3'-OCH$_3$), 51.2 (6-OCH$_3$), 157.9 (9)

Test example [Antimicrobial activity test]

The antimicrobial activity of a compound of this invention against various test bacteria was measured using sensitive disc media (produced by Eiken Chemical Co.) according to the MIC assay method of the Japan Chemotherapy Society.

Erythromycin A and 6-O-methylerythromycin A were used as comparative pharmaceuticals. The results were expressed by MIC values (minimum inhibitory concentrations on growth of the microorganisms mcg/ml) and shown in Table 1.

TABLE 1

| Name of bacterium | Sample A | Sample B | Sample C |
|---|---|---|---|
| B. subtilis ATCC6633 | 0.1 | ≦0.05 | ≦0.05 |
| S. aureus 209P-JC | 0.1 | ≦0.05 | ≦0.05 |
| S. aureus Smith 4 | 0.1 | 0.1 | 0.1 |
| S. aureus BB | 0.2 | 0.1 | ≦0.05 |
| S. epidermidis sp-al-1 | 0.2 | 0.1 | ≦0.05 |
| E. faecalis CSJ1212 | 0.78 | 0.78 | 0.39 |
| E. coli NIHJ JC-2 | 100 | 50 | 12.5 |
| E. coli CSJ1922 | 100 | 50 | 12.5 |
| E. coli K-12 | 12.5 | 12.5 | 3.13 |
| K. pneumoniae IFO3317 | 25 | 25 | 6.25 |

Notes) Among the bacteria in the table, the upper six kinds are Gram-positive bacteria, and the lower four kinds are Gram-negative bacteria. Further, samples A to C represent the following compounds.

Sample A: Erythromycin A
Sample B: 6-O-Methylerythromycin A
Sample C: Compound prepared in (2) of Example 4

Industrial Applicability

The compounds of the formula (I) of this invention have a strong antimicrobial activity not only against Gram-positive bacteria but also against Gram-negative bacteria, and are useful as an antimicrobial agent. Further, the compounds of the formula (II) are useful as intermediates of the compounds of the formula (I).

I claim:

1. A 6-O-methylerythromycin A derivative represented by the following formula

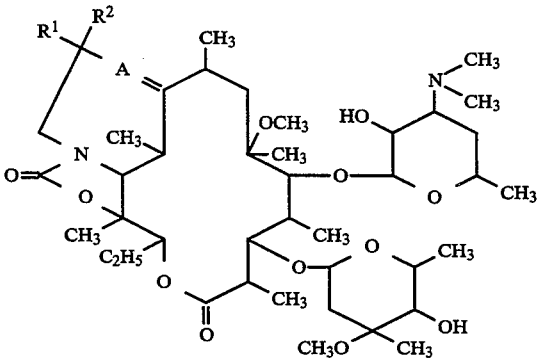

wherein R$^1$ and R$^2$ each represent a hydrogen atom or an alkyl group having 1 to 3 carbon atoms, and A represents a nitrogen atom or a N→O group or a pharmaceutically acceptable salt thereof.

* * * * *